United States Patent [19]

Moberg

[11] Patent Number: 4,530,922

[45] Date of Patent: Jul. 23, 1985

[54] FUNGICIDAL IMIDAZOLES AND TRIAZOLES CONTAINING SILICON

[75] Inventor: William K. Moberg, Wilmington, Del.

[73] Assignee: E. I. Du Pont de Nemours and Company, Wilmington, Del.

[21] Appl. No.: 567,889

[22] Filed: Jan. 3, 1984

[51] Int. Cl.[3] .......... A01N 55/00; C07F 7/10

[52] U.S. Cl. .......... 514/63; 548/110; 556/488

[58] Field of Search .......... 548/110; 424/184

[56] References Cited

U.S. PATENT DOCUMENTS

| | | | |
|---|---|---|---|
| 3,256,308 | 6/1966 | Sterling et al. | 260/448.8 |
| 3,337,598 | 8/1967 | Sterling et al. | 260/448.8 |
| 3,692,798 | 9/1972 | Barcza | 260/309 |
| 3,912,752 | 10/1975 | Meiser et al. | 260/208 |
| 4,248,992 | 2/1981 | Takago | 528/28 |
| 4,414,210 | 11/1983 | Miller et al. | 424/245 |

FOREIGN PATENT DOCUMENTS

| | | |
|---|---|---|
| 785127 | 12/1972 | Belgium . |
| 867245 | 11/1978 | Belgium . |
| 29993 | 12/1979 | European Pat. Off. . |
| 827703 | 4/1983 | South Africa . |
| 271552 | 9/1970 | U.S.S.R. . |
| 346306 | 10/1972 | U.S.S.R. . |

OTHER PUBLICATIONS

Research Disclosure 17,652 (12-1978).

Abstract of West German PN 3,000,140 (1-4-80).

*Primary Examiner*—Richard L. Raymond

[57] ABSTRACT

Silyl methyl 1,2,4-triazoles and imidazoles having broad fungicidal activity have been discovered.

18 Claims, No Drawings

FUNGICIDAL IMIDAZOLES AND TRIAZOLES CONTAINING SILICON

BACKGROUND OF THE INVENTION

The present invention relates to silicon-containing triazoles and imidazoles such as allyl[bis(4-fluorophenyl)](1H-1,2,4-triazol-1-ylmethyl)silane, and to their use in controlling fungus diseases of living plants.

U.S. Pat. No. 3,692,798 discloses compounds of the formula:

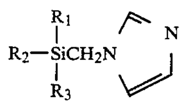

wherein $R_1$, $R_2$ and $R_3$ can be lower alkyl and phenyl. It is stated that these compounds are useful as antimicrobial agents.

European Patent Application No. 68,813 discloses compounds of the formula:

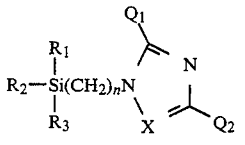

wherein n is 1;

X is N or $CQ_3$;

$Q_1$, $Q_2$ and $Q_3$ are H or $CH_3$;

$R_1$ is alkyl, cycloalkyl, naphthyl, or substituted phenyl;

$R_2$ and $R_3$ are alkyl, cycloalkyl, substituted phenyl, or $OR_6$, or together they may represent a glycol bridge; and $R_6$ is H or alkyl;

provided that both $R_2$ and $R_3$ are not OH, and their use as agricultural fungicides.

U.S.S.R. Pat. No. 346,306 discloses silylmethylazoles of the formula:

$(R_1)_n(R_2O)_{3-n}SiCH_2Az$ wherein $R_1$ and $R_2$ are alkyl groups, n is 0–3, and Az is a pyrazole, imidazole, or benzimidazole ring, optionally substituted.

U.S.S.R. Pat. No. 271,552 discloses silylethylazoles of the formula:

$(R_1)_n(R_2O)_{3-n}SiCH_2CH_2Az$ wherein $R_1$, $R_2$, n, and Az are as described in the previous reference.

European Pat. No. 11,769 teaches that compounds of the general formula:

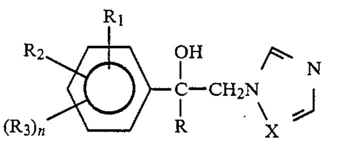

wherein

R is a substituted phenyl, naphthyl or tetrahydronaphthyl ring;

$R_1$ is a substituted phenyl or cycloalkyl ring;

$R_2$ is H, or together with $R_1$ it may form an annelated aryl or alkyl ring;

$R_3$ is halogen, alkyl, alkoxy or haloalkyl; n is 0, 1, 2 or 3; and X is CH or N, are useful as antimicrobial agents.

European Pat. No. 15,756 discloses compounds of the formula:

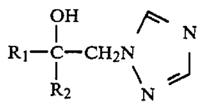

wherein $R_1$ is alkyl, cycloalkyl, or substituted phenyl; and $R_2$ is substituted phenyl or benzyl, and their use as agricultural fungicides.

European Pat. No. 36,153 discloses compounds of the formula:

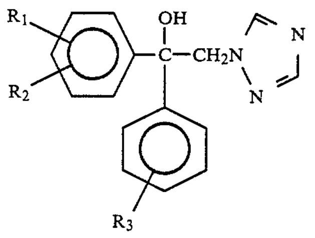

wherein $R_1$, $R_2$ and $R_3$ are H or Cl, provided that at least one of $R_1$ or $R_3$ is Cl, and their use as antimicrobials.

Belgian Pat. No. 867,245 discloses compounds of the formula:

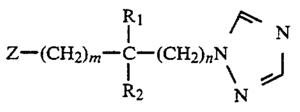

wherein

Z is aryl;

$R_1$ is CN, H, alkyl, cycloalkyl, alkenyl, cycloalkenyl, alkynyl, substituted aryl, or substituted aralkyl;

$R_2$ is H, alkyl, cycloalkyl, alkenyl, cycloalkenyl, alkynyl, substituted aryl, substituted aralkyl, alkoxy, alkenoxy, alkynoxy, OH, substituted aryloxy, or substituted aralkyloxy;

m is 0 or 1; and n is 1 or 2, and their use as agricultural fungicides.

Belgian Pat. No. 838,298 discloses compounds of the following formula:

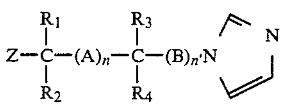

wherein

A and B are $C_1$–$C_5$ divalent alkyl groups;

$R_1$ is H, CN, alkyl, cycloalkyl, alkenyl, cycloalkenyl, alkynyl, optionally substituted aryl, or optionally substituted aralkyl;

$R_2$ is H, alkyl, alkenyl, alkynyl, cycloalkyl, cycloalkenyl, optionally substituted aryl, or optionally substituted aralkyl;

$R_3$ and $R_4$ are H, alkyl, alkenyl, cycloalkyl, cycloalkenyl, optionally substituted aryl, or optionally substituted aralkyl;

Z is optionally substituted aryl;

n is 0 or 1; and n' is 0 or 1, and their use as agricultural fungicides.

U.S. Pat. No. 4,414,210 discloses compounds of the formula:

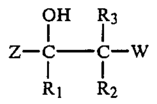

wherein

Z is an aryl or substituted aryl group;

$R_1$, $R_2$, and $R_3$ are independently H, CN, alkyl, cycloalkyl, alkenyl, alkynyl, aryl, substituted aryl, aralkyl, or substituted aralkyl; and W is a 1- or 4-(1,2,4-triazole), and their use as agricultural fungicides.

SUMMARY OF THE INVENTION

This invention relates to novel compounds of Formula I, to agriculturally useful compositions containing them, and to their method of use as fungicides.

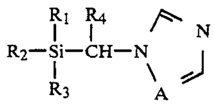

I wherein $R_1$ is H, $-CR_5{=}CHR_6$, $-CH_2CR_4{=}C(R_4)_2$, $-C{\equiv}CR_7$ or $OSi(CH_3)_3$;

$R_2$ is $C_1$-$C_6$ alkyl, vinyl or

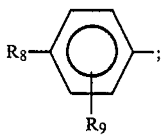

$R_3$ is $C_1$-$C_6$ alkyl,

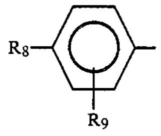

or $OR_{10}$;

$R_4$ is independently H or $CH_3$;

$R_5$ and $R_6$ are independently H, $C_1$-$C_2$ alkyl or

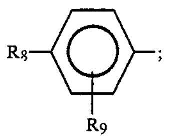

$R_7$ is H, $C_1$-$C_4$ alkyl or

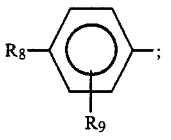

$R_8$ is H, Cl, F, Br or phenyl;

$R_9$ is H, Cl, F or Br;

$R_{10}$ is H, $C_1$-$C_4$ alkyl or

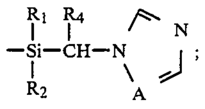

and

A is CH or N;

with the provisos that if $R_3$ is $OR_{10}$, then $R_1$ may not be H or $-OSi(CH_3)_3$;

and if $R_7$ is $C_1$-$C_4$ alkyl or phenyl, then $R_2$ may not be $C_1$-$C_6$ alkyl or vinyl.

This invention further relates to fungicidally active protic acid salts or metal complexes of compounds of Formula I.

Compounds of Formula I that are preferred for reasons of high activity and/or favorable ease of synthesis are compounds in which $R_1$ is H, $-CH{=}CH_2$, or $-CH_2{=}CH_2$;

$R_2$ and $R_3$ are independently

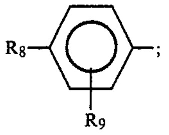

and $R_4$ is H.

Compounds of Formula I that are more preferred for reasons of high activity and/or favorable ease of synthesis are compounds of the scope immediately above, but in which $R_1$ is $-CH{=}CH_2$ or $-CH_2CH{=}CH_2$.

A specifically preferred compound is:

Allyl[bis(4-fluorophenyl)](1H-1,2,4-triazol-1-ylmethyl)silane.

DETAILED DESCRIPTION OF THE INVENTION

Synthesis

The Formula I compounds of this invention can be prepared from chloromethylsilanes of Formula II, in which $R_1$-$R_4$ are defined as in Formula I, by reacting with 1,2,4-triazole potassium salt (A is N) or with imidazole potassium salt (A is CH).

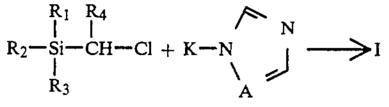

II

Sodium and lithium salts may also be used. Bromomethylsilanes, iodomethylsilanes, or arylsulfonyloxymethylsilanes may be used instead of chloromethylsilanes. Roughly equimolar amounts of the reagents are used [except when $R_1$ is —H or —$OSi(CH_3)_3$ or when $R_3$ is $OR_{10}$, as described below.] However, the triazole or imidazole salt can be used in 5–10% excess of theory. In addition, 1,2,4-triazole itself or imidazole itself can be used if an acid acceptor is used. Suitable acceptors include alkali metal alkoxides such as sodium methoxide or potassium tert-butoxide, inorganic bases such as potassium carbonate or sodium hydride, and tertiary amines such as triethylamine. When the acid acceptor is a good nucleophile, such as sodium methoxide, an excess should be avoided to prevent undesired side reactions. Suitable solvents include polar aprotic solvents such as dimethylformamide, dimethyl sulfoxide, or acetonitrile; ethers such as tetrahydrofuran or 1,2-dimethoxyethane; and ketones such as 2-butanone. Nonpolar solvents, for example aromatic hydrocarbons such as toluene, may also be used if a suitable phase transfer catalyst such as tetrabutylammonium hydrogen sulfate is added. The reaction temperature can vary between 0° and 200°, preferably between 25° and 100°. The reaction can be conducted under elevated pressure, but it is generally preferable to operate at atmospheric pressure. The optimum temperature and reaction time will vary with the concentration and choice of reagents, and especially with the choice of solvent. For compounds where $R_4$ is H, 1,2,4-triazole and sodium methoxide at roughly 2 molar concentration in dimethylformamide gives good conversion in approximately 2 hours at 80°–90°, whereas 1,2,4-triazole and potassium carbonate at roughly 1 molar in 2-butanone requires 8–12 hours at reflux. In general, reaction times of 1 to 24 hours are required when $R_4$ is H. However, longer reaction times are required if $R_4$ is methyl. For example, 1H-1,2,4-triazole sodium salt in dimethylformamide gives good conversion in approximately 64 hours at 50° C. when $R_4$ is methyl.

Those skilled in the art will recognize that the preparation of the triazole compounds of this invention can produce a mixture of two triazole isomers, the 1H-1,2,4-triazol-1-yl compound and the 4H-1,2,4-triazol-4-yl compound. Since the former isomer will be the predominant one, Formula I [A=N] is drawn to depict its structure, and the compounds will be referred to as the 1H,1yl triazoles. It is to be recognized, however, that the 4H,4yl isomer can be present, and since this isomer is also fungicidally active, no separation of the isomers is necessary after preparation of the compounds.

For the case where $R_4=OR_{10}$ in Formula I, the chlorines of a chloro(chloromethyl)silane can be replaced in one of two ways. In one method, at least two equivalents of 1,2,4-triazole sodium salt or imidazole sodium salt are used. An intermediate containing a very reactive silicon-triazole bond forms, and reaction with water or an alcohol gives the desired oxygenated compounds as shown in the following reaction sequence:

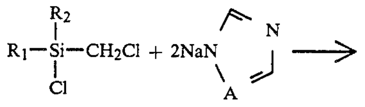

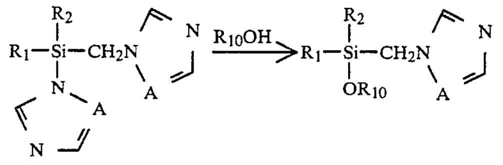

Suitable solvents and reaction conditions are the same as those outlined previously for triazole and imidazole displacements. The temperature of alcoholysis is not critical, and warming to 50°–100° can be used to ensure complete reaction when $R_{10}=C_1$–$C_4$ alkyl. For $R_{10}=H$, however, hydrolysis is best conducted near room temperature to minimize disiloxane formation, recognizing that silanol-disiloxane equilibrium is possible whenever $R_{10}=H$:

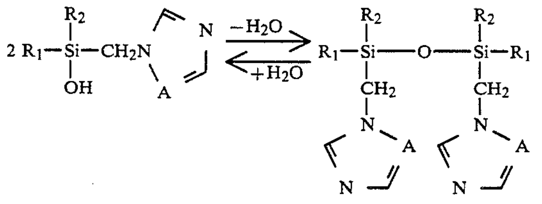

The position of equilibrium and the rate at which it is established will vary with the values of $R_1$ and $R_2$, solvent, temperature, and the presence or absence of acidic or basic catalysts.

In the second method for compounds having $R_3=OR_{10}$, the silicon-oxygen bond is formed first, followed by triazole or imidazole displacement as described earlier:

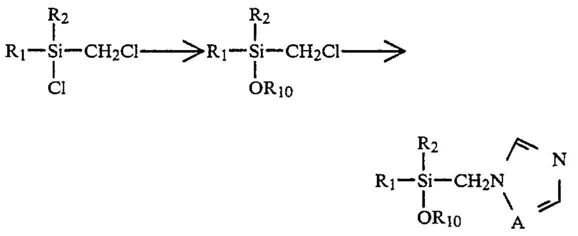

Reaction of the chlorosilane with $R_{10}OH$ may be conducted in almost any non-hydroxylic solvent, with ethers such as diethyl ether, 1,2-dimethoxyethane, and tetrahydrofuran or dipolar aprotic solvents such as dimethylformamide and acetonitrile being preferred. Although an acid acceptor is not required, it is preferred to add a tertiary amine such as triethylamine or pyridine. The reaction temperature may vary from 0° to 100°, and $R_{10}OH$ is often taken in excess of theory. The combination of 2 equivalents of $R_{10}OH$, 1.1 equivalents of triethylamine, and 0.1 equivalents of imidazole in dimethylformamide at 80° for two hours has been broadly applicable. Compounds having $R_{10}$=alkyl may be converted to silanols ($R_{10}=H$) and/or the corresponding disiloxanes by hydrolysis, catalyzed by acid or base, preferably catalyzed by acid. In some instances this cleavage may occur during the triazole displacement, so that chloromethyl silyl ethers having $R_{10}$=alkyl can give rise directly to triazolylmethyl silanols having $R_{10}$=H.

For the case where $R_1$ of Formula I is H, a chloro(-chloromethyl)silane is reacted with two equivalents of 1,2,4-triazole potassium salt or imidazole potassium salt to form the silicon-triazole or silicon-imidazole intermediate.

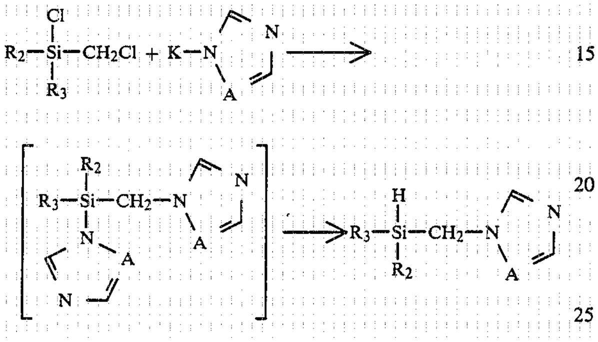

These intermediates, which contain very reactive silicon-nitrogen bonds, may be reduced, for example with diisobutylaluminum hydride, to give compounds having $R_1$=H. In this variant the solvent must be compatible with the reducing agent, and hydrocarbons such as toluene are preferred.

The compounds of Formula I in which $R_1$=O-Si$(CH_3)_3$ can be prepared by reacting chlorotrimethylsilane with compounds of Formula III, in which $R_2$-$R_4$ and A are defined as above, in the presence of a suitable acid acceptor such as triethylamine.

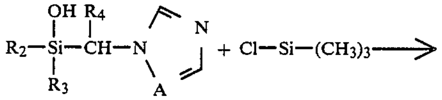

III

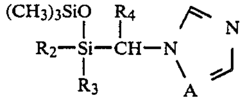

Preferred solvents for these reactions include ethers such as diethyl ether or tetrahydrofuran and polar aprotic solvents such as dimethylformamide or acetonitrile. The temperature can vary between 0° and 60° C. Compounds of Formula III can be prepared as described in European Patent Application No. 68,813.

The required chloromethylsilane starting materials are made from commercially available chloro(-chloromethyl)dimethylsilane, chloromethyl(dichloro)-methylsilane, or chloromethyltrichlorosilane:

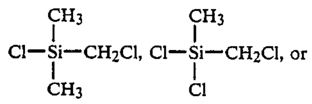

-continued

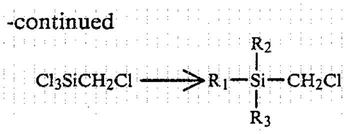

The Si—Cl bonds in these compounds react with organolithium, organosodium, or Grignard reagents to introduce alkyl, allyl, olefinic, acetylenic, and/or aryl groups according to literature procedures, leaving the C—Cl bond intact. For the silanes containing two or three Si—Cl bonds, stepwise replacements are possible, giving considerable flexibility to the values of $R_1$-$R_3$. Bromosilanes, iodosilanes, or alkoxysilanes may be substituted for chlorosilanes in these reactions. Preferred solvents for these reactions include ethers such as tetrahydrofuran, 1,2-dimethoxyethane, and diethyl ether, or hydrocarbons such as hexane and toluene. The temperature will vary between −80° and 40° depending on the nature of the organometallic reagent, how it was generated, and the solvent. For example, when aryllithium reagents are generated in tetrahydrofuran from aryl bromides using butyllithium, the mixture should be held below about −40° to avoid side reactions involving the bromobutane produced. If the organometallic solution is stable at higher temperatures, however, reactions may be run at −20° to 25° without competing reaction of the $CH_2Cl$ group.

Intermediates of Formula II wherein $R_4$ is methyl can be prepared by either of two literature methods. Free-radical chlorination of ethylchlorosilanes with sulfuryl chloride is described by Y. Nagai, N. Machida, H. Kono and T. Migita, *J. Org. Chem.*, 32, 1194 (1967). Mixtures of 1- and 2-chloroethylchlorosilanes are obtained. The 1-chloroethyl isomer can be separated, for example by distillation, and converted to the appropriately substituted 1-chloroethylsilane by Grignard addition as described above. This is illustrated as follows:

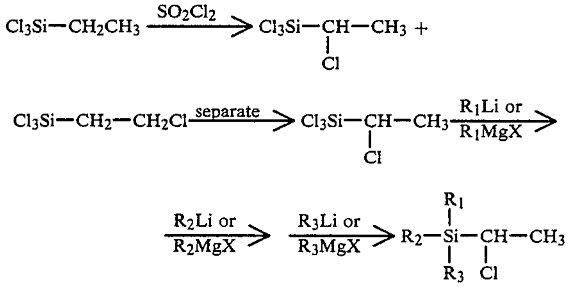

An alternative synthesis was developed using metallation chemistry. Reaction of chloromethyltrimethylsilane with secondary butyllithium and tetramethylethylenediamine (TMEDA) forming 1-lithio-1-chloromethyltrimethylsilane, followed by treatment with methyl iodide to yield 1-chloroethyltrimethylsilane, is described by C. Burford, F. Cooke, E. Ehlinger and P. Magnus, *J. Am. Chem. Soc.*, 99, 4536 (1977) and F. Cooke and P. Magnus, *J. Chem. Soc. Chem. Comm.*, 513 (1977):

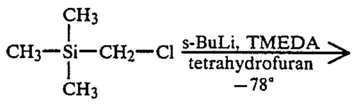

-continued

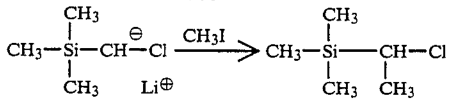

A useful modification of the literature method has been developed in the present work, extending it to more complex silanes. Deprotonation of chloromethylsilanes with sec-butyllithium followed by treatment with methyl halides has been found to give 1-chloroethylsilanes:

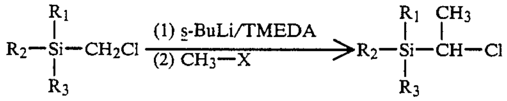

It will be recognized that the Formula II compounds can contain up to two asymmetric atoms (when $R_4$ is methyl and/or when $R_2$ is different from $R_3$), and reaction with triazole or imidazole as described above will lead to Formula I compounds also containing up to two asymmetric atoms. The stereoisomers that can result all have fungicidal activity, and separation of these isomers is not required.

In the following examples, temperatures are reported in degrees Celsius. Abbreviations for nuclear magnetic resonance (nmr) spectra are s=singlet, d=doublet, t=triplet, q=quartet, m=multiplet; peak positions are reported as parts per million downfield from internal tetramethylsilane. Infrared (ir) peak positions are given in reciprocal centimeters ($cm^{-1}$). Hexanes refers to the mixture of isomers boiling 68°-69°, and ether refers to diethyl ether.

EXAMPLE 1

Preparation of Chloromethyl(4-fluorophenyl)divinylsilane

To a solution of 6.3 ml (0.050 mol) of chloromethyltrichlorosilane in 75 ml of tetrahydrofuran cooled to −15° C. was added 25 ml of a 2.0 molar solution of p-fluorophenylmagnesium bromide (0.050 mol) at a rate that held the temperature below 0° C. The resulting suspension was stirred 30 minutes at 0° C. then allowed to warm to room temperature over 1 hour. A solution of vinylmagnesium bromide (71 ml, 1.4 molar in tetrahydrofuran) was then added, keeping the temperature below 35° C. The mixture was stirred 2 hours, then washed with saturated ammonium chloride. The aqueous layer was washed with ether-hexanes, and the combined organic layers were washed with brine, dried over sodium sulfate and evaporated. Kugelrohr distillation gave 7.25 g of the title compound as a colorless oil: nmr ($CDCl_3$) 3.1 (2H, s), 5.8-6.7 (6H, m), 7.1, 7.7 (4H, two approximate t); ir (neat) 3060, 2955, 1590, 1497, 1402, 1232, 1162, 1105, 1006, 960, 821, 768 $cm^{-1}$.

EXAMPLE 2

Preparation of Chloromethyl[bis(4-fluorophenyl)]vinylsilane

To a solution of 12.1 g (0.040 mole) of bis(4-fluorophenyl)chloromethylchlorosilane in 40 ml of tetrahydrofuran under nitrogen was added 31.4 ml of a 1.4 molar solution of vinylmagnesium bromide. The temperature rose about 20° C. The mixture was warmed to 50° C. for 3 hours, then allowed to cool to room temperature and stirred overnight. The mixture was then diluted with ether-hexanes and washed with saturated ammonium chloride. The organic layer was washed with brine and dried over sodium sulfate, and the solvents were removed in vacuo. Kugelrohr distillation (110°-125° C., 0.05 mm) gave 9.9 g of the title compound as a colorless oil: nmr ($CDCl_3$) 3.2 (2H, s), 5.5-6.7 and 6.8-7.8 (m, total 11H); ir (neat) 1590, 1500, 1240, 1175, 1115 $cm^{-1}$.

EXAMPLE 3

Preparation of Chloromethyl[bis(4-fluorophenyl)](1-hexynyl)silane

A solution of 2.9 ml (0.024 mol) of 1-hexyne in 50 ml of tetrahydrofuran under nitrogen was cooled to −5° C. A solution of n-butyllithium in hexane (15 ml of 1.6 molar, 0.024 mol) was added dropwise, and the resulting solution was warmed to room temperature and stirred for 1.5 hours. The solution was then cooled to −65° C., and a solution of 6.0 g (0.0198 mol) of bis(4-fluorophenyl)chlorochloromethylsilane in 10 ml of THF was added dropwise. The reaction was warmed to room temperature and quenched by addition of saturated aqueous ammonium chloride. The solution was partitioned between water and ether, and the organic layer was separated, washed with brine and dried over magnesium sulfate. Removal of solvent gave the title compound as a clear colorless oil: nmr ($CDCl_3$) 1.0 (3H, m), 1.5 (4H, m), 2.4 (2H, m), 3.2 (2H, s), 7.2 (4H, t, J=9 Hz), 7.7 (4H, d of d, J=9, 6 Hz); ir (neat) 2180 $cm^{-1}$.

EXAMPLE 4

Preparation of Allyl(chloromethyl)[bis(4-fluorophenyl)]silane

A mixture of 1.04 g (0.0428 mol) of magnesium turnings and about 0.05 g of iodine in 50 ml of ether was stirred under nitrogen while a solution of 4.7 ml (0.0544 mol) of 3-bromopropene in ether was added dropwise. The iodine color quickly disappeared, and the reaction temperature was kept around 30° C. by cooling with ice-water. The resulting solution was stirred 2 hours at room temperature. A solution of 10.0 gm (0.033 mol) of bis(4-fluorophenyl)chlorochloromethylsilane in 20 ml of ether was then added over 5 minutes, and the resulting mixture was allowed to stir overnight. The solution was treated with 20 ml of saturated aqueous ammonium chloride and extracted with ether. The ether was washed with water and with brine. Drying over magnesium sulfate and removal of solvent afforded a clear colorless oil which was distilled at 0.4 torr (bp 120°-130° C.) to give the title compound: nmr ($CDCl_3$) 2.3 (2H, d, J=8 Hz), 3.3 (1H, s), 5.0 (2H, m), 5.8 (1H, m), 7.1 (4H, t, J=9 Hz), 7.6 (4H, d of d, J=9,6 Hz).

EXAMPLE 5A

Preparation of 1-Chloroethyltrichlorosilane and 2-Chloroethyltrichlorosilane A mixture of 50 ml (0.38 mol) of ethyltrichlorosilane, 36.5 ml (0.45 mol) of sulfuryl chloride, and 0.62 g (3.8 mmol) of 2,2′-azobis(2-methylpropionitrile) was heated at reflux for three hours, and the contents of the reaction pot were then distilled. The fraction boiling between 130° and 155° analyzed as 29% 1-chloroethyltrichlorosilane and 71% 2-chloroethyltrichlorosilane; yield 52.48 g (70%): nmr ($CDCl_3$) 1.7 (d, J=7 Hz, 1-chloro), 2.1 (t, J=9 Hz, 2-chloro), 3.6-3.9 (m). Distillation of the product mixture through a 60-cm Vigreux column gave a fraction bp 141°-143° that analyzed as 61% 1-chloroethyltrichlorosilane and 39% 2-chloroethyltrichlorosilane. This could be used as is for conversion to compounds of this invention.

EXAMPLE 5B

Preparation of bis(4-Fluorophenyl)-1-chloroethyl(chloro)silane and bis(4-Fluorophenyl)-2-chloroethyl(chloro)silane A mixture of 15.62 g (0.64 mol) of magnesium metal, 450 ml of tetrahydrofuran and 0.5 ml of ethylene bromide was stirred at room temperature while a solution of 67 ml (0.61 mol) of 4-fluorobromobenzene in 450 ml tetrahydrofuran was added at a rate to induce and maintain reflux. The resulting mixture was refluxed one more hour and cooled in an ice-bath, 57.65 g (0.29 mol) of a 61/39 1-chloroethyltrichlorosilane/2-chloroethyltrichlorosilane mixture in 50 ml of tetrahydrofuran was added dropwise, and the mixture was refluxed for three hours, cooled, filtered, evaporated, triturated with hexanes, filtered, evaporated, and distilled, providing 38.6 g (42%) of the title compounds as a 1 to 1 mixture: bp 140°-152° (0.5 mm); nmr ($CDCl_3$) 1.6 (d, J=7 Hz, 1-chloro), 2.0 (t, J=7 Hz, 2-chloro), 3.6-4.0 (m), 6.8-7.2 (m) and 7.4-7.8 (m).

EXAMPLE 5C

Preparation of Allyl[bis(4-fluorophenyl)]-1-chloroethylsilane

A solution of 20 g (63 mmol) of a 1:1 mixture of bis(4-fluorophenyl)-1-chloroethyl(chloro)silane and bis(4-fluorophenyl)-2-chloroethyl(chloro)silane in 100 ml of tetrahydrofuran is treated dropwise with 71 ml (71 mmol) of 1.0 molar allyl magnesium bromide in tetrahydrofuran. The mixture is refluxed two hours, cooled, and diluted with saturated aqueous ammonium chloride and water. The aqueous phase is separated and extracted with ether, and the combined organic phases are washed with water and brine, dried over sodium sulfate, and evaporated to give the title compounds as a 1:1 mixture.

The compounds of Table I can be made using the procedures of Examples 1-5.

TABLE I

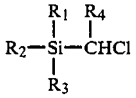

| $R_1$ | $R_2$ | $R_3$ | $R_4$ | |
|---|---|---|---|---|
| vinyl | 4-chlorophenyl | $CH_3$ | H | |
| vinyl | 4-phenylphenyl | phenyl | H | |
| vinyl | 4-phenylphenyl | $CH_3$ | H | bp 135-150° (0.06 mm) |
| vinyl | 4-fluorophenyl | $CH_3$ | H | bp 60°(0.4 mm) |
| vinyl | 4-chlorophenyl | 4-chlorophenyl | H | |
| vinyl | 2,4-dichlorophenyl | 4-fluorophenyl | H | |
| allyl | 4-chlorophenyl | 4-chlorophenyl | H | |
| allyl | 4-chlorophenyl | phenyl | H | |
| allyl | 4-fluorophenyl | phenyl | H | |
| allyl | 4-phenylphenyl | $CH_3$ | H | |
| allyl | 4-phenylphenyl | n-$C_4H_9$ | H | |
| allyl | 4-fluorophenyl | $OC_2H_5$ | H | |
| allyl | 4-fluorophenyl | t-$C_4H_9$ | H | |
| allyl | 2,4-dichlorophenyl | 4-fluorophenyl | H | |
| allyl | 2,4-dichlorophenyl | 4-chlorophenyl | H | |
| allyl | 4-fluorophenyl | 2-fluorophenyl | H | |
| allyl | 4-bromophenyl | phenyl | H | |
| allyl | 2,4-dichlorophenyl | phenyl | H | |
| 1-pentynyl | 4-phenylphenyl | $CH_3$ | H | |
| 1-butynyl | 2,4-dichlorophenyl | $CH_3$ | H | |
| 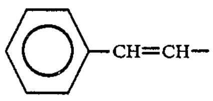 | $CH_3$ | $CH_3$ | H | bp 68°(0.03 mm) |
| 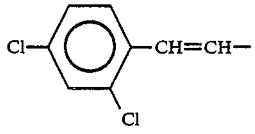 | $CH_3$ | $CH_3$ | H | |
| 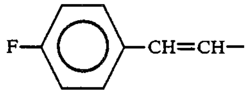 | phenyl | $CH_3$ | H | |
| 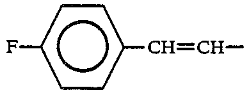 | 4-fluorophenyl | $CH_3$ | H | |

TABLE I-continued

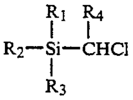

| $R_1$ | $R_2$ | $R_3$ | $R_4$ | |
|---|---|---|---|---|
| 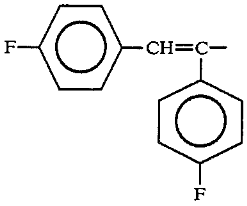 | $CH_3$ | $CH_3$ | H | |
| 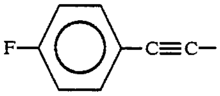 | 4-fluorophenyl | $CH_3$ | H | |
| 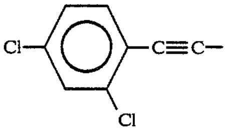 | 4-fluorophenyl | $CH_3$ | H | |
| 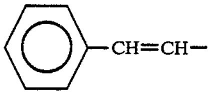 | 4-fluorophenyl | 4-fluorophenyl | H | |
| 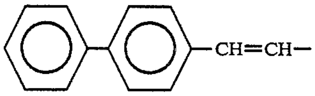 | $CH_3$ | $CH_3$ | H | |
| $(CH_3)_2C{=}CHCH_2-$ | phenyl | $i\text{-}C_3H_7O$ | H | |
| $CH_2{=}C(CH_3)-$ | 4-fluoropheny | 4-fluorophenyl | H | |
| 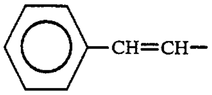 | 4-fluorophenyl | $t\text{-}C_4H_9O$ | H | |
| vinyl | vinyl | 4-phenylphenyl | H | oil |
| 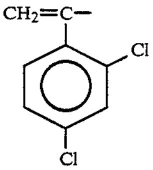 | phenyl | $CH_3$ | H | |
| vinyl | 4-fluorophenyl | 4-fluorophenyl | $CH_3$ | |
| vinyl | 4-phenylphenyl | $CH_3$ | $CH_3$ | |
| allyl | 4-fluorophenyl | 4-fluorophenyl | $CH_3$ | |
| allyl | 4-chlorophenyl | 4-chlorophenyl | $CH_3$ | |
| allyl | 2,4-dichlorophenyl | phenyl | $CH_3$ | |
| allyl | 4-phenylphenyl | $CH_3$ | $CH_3$ | |
| allyl | 4-bromophenyl | $t\text{-}C_4H_9O$ | $CH_3$ | |
| 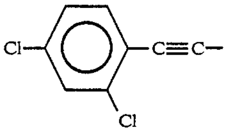 | $n\text{-}C_4H_9$ | 4-fluorophenyl | $CH_3$ | |

TABLE I-continued

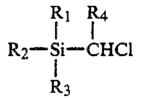

| $R_1$ | $R_2$ | $R_3$ | $R_4$ |
|---|---|---|---|
| 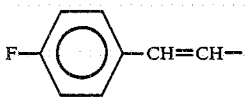 | 4-fluorophenyl | $CH_3$ | $CH_3$ |
| 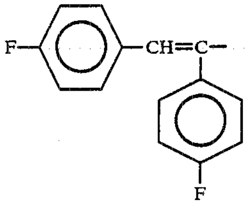 | $CH_3$ | $CH_3$ | $CH_3$ |
| vinyl | vinyl | 4-phenylphenyl | $CH_3$ |

EXAMPLE 6

Preparation of Allyl[bis(4-fluorophenyl)](1H-1,2,4-triazol-1-ylmethyl)-silane A mixture of 4.5 g (0.0146 mol) of (allyl)chloromethyl[bis(4-fluorophenyl)silane, 2.1 g (0.0196 mol) of potassium triazole, and 0.3 g of tetrabutylammonium bromide in 50 ml of toluene was heated at reflux under nitrogen for 4 hours. The solution was diluted with ethyl acetate and washed twice with water and once with brine. Drying over magnesium sulfate and removal of solvent afforded a viscous oil which was chromatographed on silica gel (10:1 methylene chloride-acetone) to afford the title compound as a clear, colorless oil: nmr ($CD_2Cl_2$) 2.3 (2H, d, J=8 Hz), 4.3 (2H, s), 5.0 (2H, m), 5.8 (1H, m), 7.1 (4H, t, J=9 Hz), 7.6 (4H, d of d, J=9,6 Hz), 7.8 (1H, s), 7.9 (1H, s).

EXAMPLE 7

Preparation of [bis(4-Fluorophenyl)](1H-1,2,4-triazol-1-ylmethyl)silane

To a solution of 3.0 g (9.9 mmol) of bis(4-fluorophenyl)chlorochloromethylsilane and 50 mg of tetrabutylammonium hydrogen sulfate in 10 ml of toluene was added 2.2 g (20.5 mmol) of potassium triazole. The resulting exotherm was controlled by cooling with ice-water. The solution was heated at reflux for 5 hours and then was cooled to −70° C. A solution of 10.5 ml (10.5 mmol) of diisobutylaluminum hydride (1.0 mol) in tetrahydrofuran was then added dropwise, and the reaction mixture was warmed to room temperature and quenched by dropwise addition of saturated aqueous ammonium chloride. The solution was diluted with methylene chloride and washed three times with water and once with brine. Drying over magnesium sulfate and removal of solvent gave a viscous oil which was chromatographed (ether) on silica gel to afford 1.0 gm (33%) of the title compound as a clear colorless oil which solidified on standing, m.p. 49°-52° C.; nmr ($CDCl_3$) 4.35 (2H, d, J=3 Hz), 5.3 (1H, t, J=3 Hz), 7.2 (4H, t, J=9 Hz), 7.6 (4H, d of d, J=9,6 Hz), 7.9 (1H, s), 8.0 (1H, s).

EXAMPLE 8

Preparation of [bis(4-Fluorophenyl)](trimethylsilyloxy)(1H-1,2,4-triazol-1-ylmethyl)silane To a solution of 1.5 g (0.0047 mol) of [bis(4-fluorophenyl)]hydroxy(1H-1,2,4-triazol-1-ylmethyl)silane in 20 ml of tetrahydrofuran was added 0.8 ml (0.0063 mol) of chlorotrimethylsilane. A solution of 0.8 ml (0.0057 mol) of triethylamine in 5 ml of tetrahydrofuran was added dropwise, giving a thick white precipitate. The mixture was stirred overnight at room temperature, then filtered and concentrated to an oil. The residue was taken up in ether, filtered, and the filtrate was evaporated to afford the title compound as a clear colorless oil: nmr ($CDCl_3$) 0.1 (9H, s), 4.3 (2H, s), 7.2 (4H, t, J=9 Hz), 7.6 (4H, d of d, J=9,6 Hz), 8.0 (2H, s).

EXAMPLE 9

Preparation of Allyl[bis(4-fluorophenyl)][1-(1H-1,2,4-triazol-1-yl)ethyl]silane A mixture of 1.78 g (37 mmol) of 50% sodium hydride, 30 ml of dimethylformamide, and 2.56 g (37 mmol) of 1H-1,2,4-triazole is stirred at 50° for one hour, and a solution of 10 g (33.7 mmol) of a 1:1 mixture of allyl[bis(4-fluorophenyl)]-1-chloroethylsilane and allyl[-bis(4-fluorophenyl)]-2-chloroethylsilane in 10 ml of dimethylformamide is added. The mixture is stirred at 50° for 64 hours, cooled, diluted with water, and extracted with ether. The ether extracts are washed with water and brine, dried over sodium sulfate, and evaporated to leave a viscous oil. Chromatography over silica gel eluting with 4:1 dichloromethane-acetone provides the title compound.

The compounds of Table II can be made using the procedures of Examples 6-9.

TABLE II

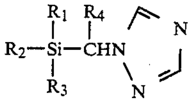

| $R_1$ | $R_2$ | $R_3$ | $R_4$ | |
|---|---|---|---|---|
| vinyl | 4-chloro-phenyl | $CH_3$ | H | |
| vinyl | 4-phenyl-phenyl | phenyl | H | |
| vinyl | 4-phenyl-phenyl | $CH_3$ | H | $n_D^{25}$ 1.6027 |
| vinyl | 4-fluoro-phenyl | $CH_3$ | H | bp 100–110° (0.1 mm) |
| vinyl | 4-chloro-phenyl | 4-chloro-phenyl | H | |
| vinyl | 2,4-dichloro-phenyl | 4-fluoro-phenyl | H | |
| allyl | 4-chloro-phenyl | 4-chloro-phenyl | H | |
| allyl | 4-chloro-phenyl | phenyl | H | |
| allyl | 4-fluoro-phenyl | phenyl | H | |
| allyl | 4-phenyl-phenyl | $CH_3$ | H | |
| allyl | 4-phenyl-phenyl | $n-C_4H_9$ | H | |
| allyl | 4-fluoro-phenyl | $OC_2H_5$ | H | |
| allyl | 4-fluoro-phenyl | $t-C_4H_9$ | H | |
| allyl | 2,4-dichloro-phenyl | 4-fluoro-phenyl | H | |
| allyl | 2,4-dichloro-phenyl | 4-chloro-phenyl | H | |
| allyl | 4-fluoro-phenyl | 2-fluoro-phenyl | H | |
| allyl | 4-bromo-phenyl | phenyl | H | |
| allyl | 2,4-dichloro-phenyl | phenyl | H | |
| 1-pentynyl | 4-phenyl-phenyl | $CH_3$ | H | |
| 1-butynyl | 2,4-dichloro-phenyl | $CH_3$ | H | |
| 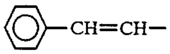 | $CH_3$ | $CH_3$ | H | $n_D^{25}$ 1.5659 |
| 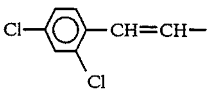 | $CH_3$ | $CH_3$ | H | |
| 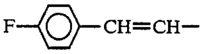 | phenyl | $CH_3$ | H | |
| 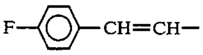 | 4-fluoro-phenyl | $CH_3$ | H | |
| 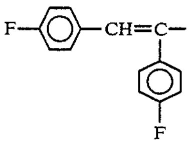 | $CH_3$ | $CH_3$ | H | |
| 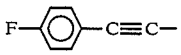 | 4-fluoro-phenyl | $CH_3$ | H | |

TABLE II-continued

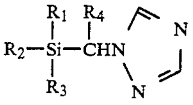

| $R_1$ | $R_2$ | $R_3$ | $R_4$ | |
|---|---|---|---|---|
| 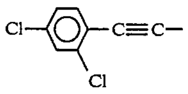 | 4-fluoro-phenyl | $CH_3$ | H | |
| 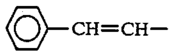 | 4-fluoro-phenyl | 4-fluoro-phenyl | H | |
| 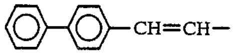 | $CH_3$ | $CH_3$ | H | |
| $(CH_3)_2C{=}CHCH_2-$ | phenyl | $i-C_3H_7O$ | H | |
| $CH_2{=}C(CH_3)-$ | 4-fluoro-phenyl | 4-fluoro-phenyl | H | |
| 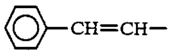 | 4-fluoro-phenyl | $t-C_4H_9O$ | H | |
| vinyl | vinyl | 4-phenyl-phenyl | H | $n_D^{23}$ 1.6143 |
| 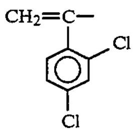 | phenyl | $CH_3$ | H | |
| vinyl | 4-fluoro-phenyl | 4-fluoro-phenyl | $CH_3$ | |
| vinyl | 4-phenyl-phenyl | $CH_3$ | $CH_3$ | |
| allyl | 4-fluoro-phenyl | 4-fluoro-phenyl | $CH_3$ | |
| allyl | 4-chloro-phenyl | 4-chloro-phenyl | $CH_3$ | |
| allyl | 2,4-dichloro-phenyl | phenyl | $CH_3$ | |
| allyl | 4-phenyl-phenyl | $CH_3$ | $CH_3$ | |
| allyl | 4-bromo-phenyl | $t-C_4H_9O$ | $CH_3$ | |
| 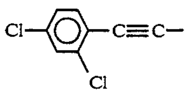 | $n-C_4H_9$ | 4-fluoro-phenyl | $CH_3$ | |
| 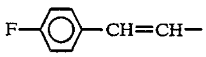 | 4-fluoro-phenyl | $CH_3$ | $CH_3$ | |
| 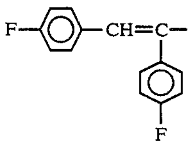 | $CH_3$ | $CH_3$ | $CH_3$ | |
| vinyl | vinyl | 4-phenyl-phenyl | $CH_3$ | |
| vinyl | 4-fluoro-phenyl | 4-fluoro-phenyl | H | $n_D^{25}$ 1.5654 |
| vinyl | vinyl | 4-fluoro-phenyl | H | bp 80–90° (0.9 mm) |
| 1-hexynyl | 4-fluoro-phenyl | 4-fluoro-phenyl | H | oil |
| $(CH_3)_3SiO-$ | 4-chloro- | 4-chloro- | H | |

TABLE II-continued

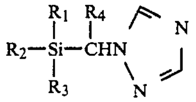

| $R_1$ | $R_2$ | $R_3$ | $R_4$ | |
|---|---|---|---|---|
| | phenyl | phenyl | | |
| $(CH_3)_3SiO$— | 4-fluoro-phenyl | 2-fluoro-phenyl | H | |
| $(CH_3)_3SiO$— | 4-bromo-phenyl | n-$C_4H_9$ | H | |
| $(CH_3)_3SiO$— | 2,4-dichloro-phenyl | phenyl | $CH_3$ | |
| H | phenyl | $CH_3$ | H | $n_D^{20}$ 1.5523 |
| H | 2-chloro-phenyl | 2-chloro-phenyl | H | m. 62-66° |
| H | 4-fluoro- | 4-phenyl-phenyl | H | |
| H | $CH_3$ | 4-phenyl-phenyl | H | |
| H | $C_2H_5$ | 4-phenyl-phenyl | $CH_3$ | |

EXAMPLE 10

Preparation of [bis(4-Fluorophenyl)](1H-imidazol-1-ylmethyl)silane

To a solution of 3.0 g (9.9 mmol) of bis(4-fluorophenyl)chlorochloromethylsilane and 50 mg of tetrabutylammonium hydrogen sulfate in 10 ml of toluene is added 2.2 g (20.5 mmol) of potassium imidazole. The resulting exotherm is controlled by cooling with ice-water. Th solution is heated at reflux for 5 hours and then was cooled to −70° C. A solution of 10.5 ml (10.5 mmol) of diisobutylaluminum hydride (1.0 molar) in tetrahydrofuran is then added dropwise, and the reaction is warmed to room temperature and quenched by dropwise addition of saturated aqueous ammonium chloride. The solution is diluted with methylene chloride and washed three times with water and once with brine. Drying over magnesium sulfate and removal of solvent gives a viscous oil which is triturated with ether to give the title compound.

EXAMPLE 11

Preparation of Divinyl(1H-imidazol-1-ylmethyl)(4-phenylphenyl)silane

To a solution of 1.14 g (0.004 mol) of chloromethyl(4-phenylphenyl)divinylsilane in 10 ml of toluene is added 0.54 g (0.005 mol) of potassium imidazole and 0.05 g of tetrabutylammonium bromide. The mixture is refluxed under nitrogen for two days, cooled, diluted with ether-hexanes, and washed with water and brine. Removal of solvent gives an oil which is purified by silica gel chromatography, eluting with 9:1 dichloromethane-ether, to give the title compound.

EXAMPLE 12

Preparation of [bis(4-Fluorophenyl)](trimethylsilyloxy)(1H-imidazol-1-ylmethy)silane To a solution of 1.5 g (0.0047 mol) of bis(4-fluorophenyl)hydroxy(1H-imidazol-1-ylmethyl)silane in 20 ml of tetrahydrofuran was added 0.8 ml (0.0063 mol) of chlorotrimethylsilane. A solution of 0.8 ml (0.0057 mol) of triethylamine in 5 ml of tetrahydrofuran is added dropwise, giving a thick white precipitate. The mixture is stirred overnight at room temperature, then filtered and concentrated to an oil. The residue is taken up in ether, filtered, and the filtrate is evaporated to afford the title compound.

The compounds of Table III can be made using the procedures of Examples 10–12.

TABLE III

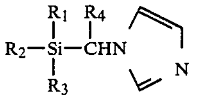

| $R_1$ | $R_2$ | $R_3$ | $R_4$ |
|---|---|---|---|
| vinyl | 4-chlorophenyl | $CH_3$ | H |
| vinyl | 4-phenylphenyl | phenyl | H |
| vinyl | 4-phenylphenyl | $CH_3$ | H |
| vinyl | 4-fluorophenyl | $CH_3$ | H |
| vinyl | 4-chlorophenyl | 4-chloro-phenyl | H |
| vinyl | 2,4-dichlorophenyl | 4-fluoro-phenyl | H |
| allyl | 4-chlorophenyl | 4-chloro-phenyl | H |
| allyl | 4-chlorophenyl | phenyl | H |
| allyl | 4-fluorophenyl | phenyl | H |
| allyl | 4-phenylphenyl | $CH_3$ | H |
| allyl | 4-phenylphenyl | n-$C_4H_9$ | H |
| allyl | 4-fluorophenyl | $OC_2H_5$ | H |
| allyl | 4-fluorophenyl | t-$C_4H_9$ | H |
| allyl | 2,4-dichlorophenyl | 4-fluoro-phenyl | H |
| allyl | 2,4-dichlorophenyl | 4-chloro-phenyl | H |
| allyl | 4-fluorophenyl | 2-fluoro-phenyl | H |
| allyl | 4-bromophenyl | phenyl | H |
| allyl | 2,4-dichlorophenyl | phenyl | H |
| 1-pentynyl | 4-phenylphenyl | $CH_3$ | H |
| 1-butynyl | 2,4-dichlorophenyl | $CH_3$ | H |
| 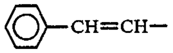 | $CH_3$ | $CH_3$ | H |
| 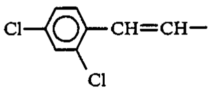 | $CH_3$ | $CH_3$ | H |
| 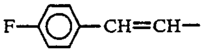 | phenyl | $CH_3$ | H |
| 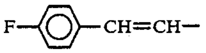 | 4-fluorophenyl | $CH_3$ | H |
| 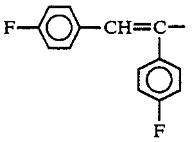 | $CH_3$ | $CH_3$ | H |
| 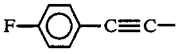 | 4-fluorophenyl | $CH_3$ | H |
| 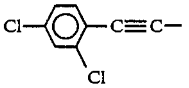 | 4-fluorophenyl | $CH_3$ | H |
| 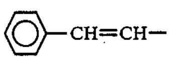 | 4-fluorophenyl | 4-fluoro-phenyl | H |

TABLE III-continued

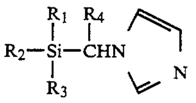

| R1 | R2 | R3 | R4 |
|---|---|---|---|
| 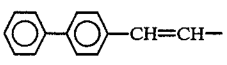 | $CH_3$ | $CH_3$ | H |
| $(CH_3)_2C{=}CHCH_2-$ | phenyl | i-$C_3H_7O$ | H |
| $CH_2{=}C(CH_3)-$ | 4-fluorophenyl | 4-fluoro-phenyl | H |
| 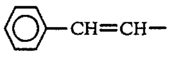 | 4-fluorophenyl | t-$C_4H_9O$ | H |
| vinyl | vinyl | 4-phenyl-phenyl | H |
| 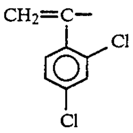 | phenyl | $CH_3$ | H |
| vinyl | 4-fluorophenyl | 4-fluoro-phenyl | $CH_3$ |
| vinyl | 4-phenylphenyl | $CH_3$ | $CH_3$ |
| allyl | 4-fluorophenyl | 4-fluoro-phenyl | $CH_3$ |
| allyl | 4-chlorophenyl | 4-chloro-phenyl | $CH_3$ |
| allyl | 2,4-dichlorophenyl | phenyl | $CH_3$ |
| allyl | 4-phenylphenyl | $CH_3$ | $CH_3$ |
| allyl | 4-bromophenyl | t-$C_4H_9O$ | $CH_3$ |
| 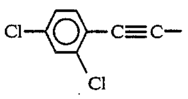 | n-$C_4H_9$ | 4-fluoro-phenyl | $CH_3$ |
| 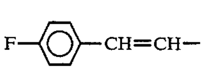 | 4-fluorophenyl | $CH_3$ | $CH_3$ |
| 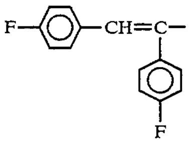 | $CH_3$ | $CH_3$ | $CH_3$ |
| vinyl | vinyl | 4-phenyl-phenyl | $CH_3$ |
| vinyl | 4-fluorophenyl | 4-fluoro-phenyl | H |
| vinyl | vinyl | 4-fluoro-phenyl | H |
| 1-hexynyl | 4-fluorophenyl | 4-fluoro-phenyl | H |
| $(CH_3)_3SiO-$ | 4-chlorophenyl | 4-chloro-phenyl | H |
| $(CH_3)_3SiO-$ | 4-fluorophenyl | 4-fluoro-phenyl | H |
| $(CH_3)_3SiO-$ | 4-bromophenyl | n-$C_4H_9$ | H |
| $(CH_3)_3SiO-$ | 2,4-dichlorophenyl | phenyl | $CH_3$ |
| H | phenyl | $CH_3$ | H |
| H | 2-chlorophenyl | 2-chloro-phenyl | H |
| H | 4-fluorophenyl | 4-phenyl-phenyl | H |
| H | $CH_3$ | 4-phenyl-phenyl | H |
| H | $C_2H_5$ | 4-phenyl- | $CH_3$ |

TABLE III-continued

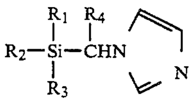

| R1 | R2 | R3 | R4 |
|---|---|---|---|
| | | phenyl | |

UTILITY

The compounds of this invention are useful as plant disease control agents. They are effective in controlling a broad spectrum of plant diseases, particularly foliar pathogens of ornamental, vegetable, field, cereal and fruit crops, such as, *Puccinia recondita, Sphaerotheca fuliginea, Erysiphe graminis, Podosphaera leucotricha, Venturia inaequalis, Pyricularia oryzae, Bipolaris oryzae, Cercospora arachidicola, Cercospora beticola* and *Monilinia fructicola.* They also control soil borne pathogens such as *Rhizoctonia solani.*

FORMULATION AND USE

The compounds of this invention will generally be used in formulation with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid inert diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20-90 | 0-74 | 1-10 |
| Oil Suspensions, Emulsions Solutions, (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084), Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1-4.

G. C. Klingman, "Weed Control as a Science", John Wiley and Sons, Inc., New York, 1961, pp. 81-96.

J. D. Fryer and S. A. Evans, "Weed Control Handbook", 5th Edn. Blackwell Scientific Publications, Oxford, 1968, pp. 101-103.

Examples of useful formulations of compounds of the present invention are as follows.

EXAMPLE 13

| Wettable Powder | |
|---|---|
| [bis(4-Chlorophenyl)](1H—1,2,4-triazol-1-ylmethyl)-silane | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, re-blended and packaged.

EXAMPLE 14

| High Strength Concentrate | |
|---|---|
| [bis(4-Fluorophenyl)](1H—1,2,4-triazol-1-ylmethyl)-silane | 98.5% |
| silica aerogel | 0.5% |
| synthetic amorphous fine silica | 1.0% |

The ingredients are blended and ground in a hammer-mill to produce a high strength concentrate essentially all passing a U.S.S. No. 50 sieve (0.3 mm openings). This material may then be formulated in a variety of ways.

EXAMPLE 15

| Aqueous Suspension | |
|---|---|
| Divinyl(4-phenylphenyl)(1H—1,2,4-triazol-1-ylmethyl)-silane | 25% |
| hydrated attapulgite | 3% |
| crude calcium ligninsulfonate | 10% |
| sodium dihydrogen phosphate | 0.5% |
| water | 61.5% |

The ingredients are ground together in a ball, sand, or roller mill until the solid particles have been reduced to diameters under 10 microns.

EXAMPLE 16

| Solution | |
|---|---|
| Allyl[bis(4-fluorophenyl)](1H—1,2,4-triazol-1-yl-methyl)silane | 30% |
| dimethylformamide | 70% |

The ingredients are combined and stirred to produce a solution, which can be used for low volume applications.

EXAMPLE 17

| Emulsifiable Concentrate | |
|---|---|
| Allyl[bis(4-fluorophenyl)](1H—1,2,4-triazol-1-yl-methyl)silane | 30% |
| blend of oil soluble sulfonates and polyoxyethylene ethers | 4% |
| xylene | 66% |

The ingredients are combined and stirred until the active is dissolved. A fine screen filter is included in packaging operation to insure the absence of any extraneous undissolved material in the product.

EXAMPLE 18

| Granule | |
|---|---|
| wettable powder of Example 13 | 15% |
| gypsum | 69% |
| potassium sulfate | 16% |

The ingredients are blended in a rotating or fluid bed mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range. These granules contain 12% active ingredient.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl(4,4'-o-phenylene)bis(3-thioallophanate) (thiophanate-methyl)
2-(thiazol-4-yl)benzimidazole (thiabendazole)
aluminum tris(O-ethyl phosphonate) ("Aliette")
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[(1,1,2,2-tetrachloroethyl)thio]-4-cyclohexene-1,2-dicarbioximide (captafol)
3-(3,5-dichlorophenyl)-N-(1-methyl-ethyl)-2,4-dioxo-1-imidazolidine carboxamide (iprodione)
3-(3,5-dichlorophenyl)-5-ethenyl-5-methyl-2,4-oxazolidinedione (vinclozolin) kasugamycin
O-ethyl S,S-diphenyl phosphorodithioate (edifenphos)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-β]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematicides

2-[diethoxyphosphinylimino]-1,3-dithietane (fosthietan)
S-methyl-1-(dimethylcarbamoyl)-N-(methylcarbamoyloxy)thioformimidate (oxamyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-O-(2-isopropyl-4-methyl-6-pyrimidyl)-phosphorothioate (diazinon)
octachlorocamphene (toxaphene)
O-ethyl O-p-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl(±)-cis,trans-3-(2,2-dichloroethenyl)-2,2-dimethylcyclopropanecarboxylate (permethrin)
dimethyl[N,N'-[thiobis][(N-methylimino)carbonyloxy]]bis[ethanimidothioate] (thiodicarb)
phosphorothiolothionic acid, O-ethyl-O-[4-(methylthio)phenyl]-S-n-propyl ester (sulprofos)
α-cyano-3-phenoxybenzyl 3-(2,2-dichlorovinyl)-2,2-dimethylcyclopropane carboxylate (cypermethrin)
cyano(3-phenoxyphenyl)methyl 4-(difluoromethoxy)-α-(methylethyl)benzeneacetate ("Payoff")
O,O-diethyl-O-(3,5,6-trichloro-2-pyridyl)phosphorothioate (chlorpyrifos)
O,O-dimethyl-S-[(4-oxo-1,2,3-benzotriazin-3-(4H)-yl)methyl]phosphorodithioate (azinphos-methyl)
5,6-dimethyl-2-dimethylamino-4-pyrimidinyl dimethyl carbamate ("Pirimor")
S-(N-formyl-N-methylcarbamoylmethyl-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (fluvalinate)

APPLICATION

Disease control is ordinarily accomplished by applying an effective amount of the compound, normally as part of a formulation containing it, either pre- or post-infection to the portion of the plant to be protected, such as the roots, stems, foliage, fruit, seeds, tubers or bulbs, or to the medium (soil or sand) in which the plants to be protected are growing. The compound may also be applied to the seed from which the plants to be protected are to be grown.

Rates of application for these compounds can be influenced by many factors of the environment and should be determined under actual use conditions. Nevertheless, foliage can normally be protected when treated at a rate of from 1 gram or less up to 5000 grams of active ingredient per hectare. Plants growing in soil that is treated at a concentration from about 0.1 to about 20 kg of active ingredient per hectare can be protected from disease. Seed and seedlings can normally be protected when seed is treated at a rate of from about 0.06 to about 3 grams of active ingredient per kilogram of seed.

In the following Examples 19–26, the percent disease control is determined as the percent growth inhibition of colonies on treated plants as compared to untreated plants. In these examples, which further illustrate the present invention, the test compounds are:

| Cmpd. No. | |
|---|---|
| 1 | [bis(4-Fluorophenyl)-1-hexynyl-(1H—1,2,4-triazol-1-ylmethyl)silane |

-continued

| Cmpd. No. | |
|---|---|
| 2 | Allyl[bis(4-fluorophenyl)](1H—1,2,4-triazol-1-yl-methyl)silane |
| 3 | [bis(4-Fluorophenyl)](1H—1,2,4-triazol-1-yl-methyl)(trimethylsilyloxy)silane |
| 4 | [bis(4-Fluorophenyl)](1H—1,2,4-triazol-1-yl-methyl)silane |
| 5 | [bis(4-Chlorophenyl)](1H—1,2,4-triazol-1-yl-methyl)silane |
| 6 | Methyl(phenyl)(1H—1,2,4-triazol-1-ylmethyl)silane |
| 7 | Dimethyl(1H—1,2,4-triazol-1-ylmethyl)vinylsilane |
| 8 | 4-Fluorophenyl(methyl)(1H—1,2,4-triazol-1-yl-methyl)vinylsilane |
| 9 | Dimethyl(2-phenylvinyl)(1H—1,2,4-triazol-1-yl-methyl)silane |
| 10 | [bis(4-Fluorophenyl)](1H—1,2,4-triazol-1-yl-methyl)vinylsilane |
| 11 | Methyl(4-phenylphenyl)(1H—1,2,4-triazol-1-yl-methyl)vinylsilane |
| 12 | Divinyl(4-fluorophenyl)(1H—1,2,4-triazol-1-yl-methyl)silane |
| 13 | Divinyl(4-phenylphenyl)(1H—1,2,4-triazol-1-yl-methyl)silane |

Results for Examples 19–25 are given in Table IV and results for Example 26 are given in Table V. In the tables, a rating of 100 indicates 100% disease control and a rating of 0 indicates no disease control relative to the controls. An NT entry indicates that no test was performed with the specified compound.

EXAMPLE 19

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on wheat seedlings. The following day, the plants were inoculated with a spore suspension of *Puccinia recondita* var. *tritici,* causal agent of wheat leaf rust, and incubated in a saturated humidity chamber at 20° for 24 hours and then in a growth room for an additional 7 days, when disease ratings were made.

EXAMPLE 20

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on cucumber seedlings. The following day, the plants were inoculated with a spore suspension of the fungus *Sphaerotheca fuliginea,* causal agent of cucumber powdery mildew, and incubated in a growth room for 7 days. Disease ratings were then made.

EXAMPLE 21

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on apple seedlings. The following day, the plants were inoculated with a spore suspension of the fungus *Venturia inaequalis,* causal agent of apple scab, and incubated in a saturated humidity chamber at 20° for 24 hours and then in a growth room for an additional 10–12 days. Disease ratings were then made.

EXAMPLE 22

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on corn seedlings. The following day, the plants were inoculated with a spore suspension of *Bipolaris oryzae,* causal agent of rice brown leaf spot, and incubated in a saturated humidity chamber at 20° for 24 hours and then in a growth room for an additional 7 days, after which disease ratings were made.

EXAMPLE 23

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on peanut seedlings. The following day, the plants were inoculated with a spore suspension of *Cercospora arachidicola,* causal agent of peanut early leafspot, and incubated in a saturated humidity chamber at 27° for 24 hours and then in a growth room for an additional 14 days, when disease ratings were made.

EXAMPLE 24

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on peanut seedlings. The following day, the plants were inoculated with a spore suspension of *Cercosporidium personatum,* causal agent of peanut late leafspot, and incubated in a saturated humidity chamber at 27° for 24 hours and then in a growth room for an additional 14 days, when disease ratings were made.

EXAMPLE 25

The test compounds were dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on rice seedlings. The following day, the plants were inoculated with a mixture of bran and the mycelium of the fungus *Rhizoctonia solani,* causal agent of sheath blight of rice, and incubated in a growth room for 7 days. Disease ratings were then made.

EXAMPLE 26

The test compounds were dissolved in acetone so that 1 ml of solution yielded a concentration of 0.5 kilogram/hectare when added to cotton seeds and soil in pots. Seeds and soil were then inoculated with a mixture of sand, cereal and mycelium of the fungus *Rhizoctonia solani,* causal agent of cotton blight, and incubated in a growth room for 14 days. Disease ratings were then made.

TABLE IV

| | | | | Foliar Tests at 93 grams of active ingredient per hectare | | | |
|---|---|---|---|---|---|---|---|
| Cpd # | Ex. 19 *Puccinia recondita* var. *tritici* (wheat) | Ex. 20 *Sphaerotheca fuliginea* (cucumber) | Ex. 21 *Ventura inaequalis* (apple) | Ex. 22 *Bipolaris oryzae* (rice) | Ex. 23 *Cercospora arachidicola* (peanut) | Ex. 24 *Cercosporidium personatum* (peanut) | Ex. 25 *Rhizoctonia solani* (rice) |
| 1 | 80 | 80 | 0 | 0 | NT | 85 | 0 |
| 2 | 100 | 100 | 100 | 90 | NT | 100 | 90 |
| 3 | 100 | 100 | 100 | 50 | NT | 100 | 0 |
| 4 | 80 | 100 | 100 | 98 | 100 | 100 | 0 |
| 5 | 0 | 100 | 100 | 0 | 100 | NT | 0 |
| 6 | 0 | 100 | 0 | 0 | NT | 0 | 0 |
| 7 | 0 | 100 | 0 | 0 | NT | 0 | 0 |
| 8 | 90 | 100 | 80 | 0 | 98 | 100 | 0 |
| 9 | 0 | 100 | 100 | 20 | NT | 0 | 0 |
| 10 | 100 | 100 | 100 | 90 | NT | 100 | 40 |
| 11 | 100 | 100 | 100 | 100 | NT | 100 | 90 |
| 12 | NT | 0 | 80 | 0 | NT | 0 | NT |
| 13 | 100 | 100 | 100 | 100 | NT | NT | 90 |

TABLE V

| | Soil-borne tests at 5 kg active ingredient per hectare |
|---|---|
| Cpd. # | Ex. 26 *Rhisoctonia solani* (cotton) |
| 1 | NT |
| 2 | NT |
| 3 | NT |
| 4 | 0 |
| 5 | 0 |
| 6 | 0 |
| 7 | 0 |
| 8 | 100 |
| 9 | 0 |
| 10 | 0 |
| 11 | 50 |
| 12 | 0 |
| 13 | 0 |

What is claimed is:

1. A compound of the formula:

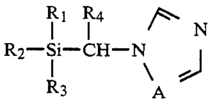

wherein $R_1$ is H, $-CR_5=CHR_6$, $-CH_2CR_4=C(R_4)_2$, $-C\equiv CR_7$ or $OSi(CH_3)_3$;

$R_2$ is $C_1$–$C_6$ alkyl, vinyl or

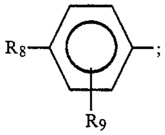

$R_3$ is $C_1$–$C_6$ alkyl,

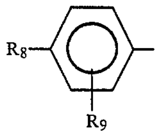

or $OR_{10}$;

$R_4$ is independently H or $CH_3$;

$R_5$ and $R_6$ are independently H, $C_1$–$C_2$ alkyl or

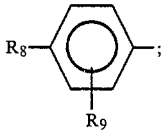

$R_7$ is H, $C_1$–$C_4$ alkyl or

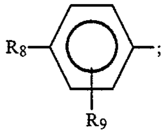

$R_8$ is H, Cl, F, Br or phenyl;

$R_9$ is H, Cl, F or Br;

$R_{10}$ is H, $C_1$–$C_4$ alkyl or

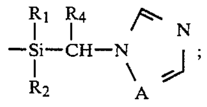

and

A is CH or N;

with the provisos that if $R_3$ is $OR_{10}$, then $R_1$ may not be H or $-OSi(CH_3)_3$;

if $R_7$ is $C_1$–$C_4$ alkyl or phenyl, then $R_2$ may not be $C_1$–$C_6$ alkyl or vinyl; and when A is CH, then at least one of $R_2$ and $R_3$ is

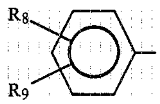

and at least one of $R_8$ and $R_9$ is other than H; and fungicidally active protic acid salts or metal complexes of said compound.

2. A compound of claim 1 wherein
$R_1$ is H, $-CH=CH_2$, or $-CH_2CH=CH_2$;
$R_2$ and $R_3$ are independently

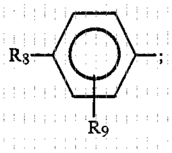

and
$R_4$ is H.

3. A compound of claim 2 wherein $R_1$ is $-CH=CH_2$ or $-CH_2CH=CH_2$.

4. A compound of claim 3 wherein A is CH.

5. A compound of claim 3 wherein A is N.

6. The compound of claim 1 that is allyl[bis(4-fluorophenyl)]1H-1,2,4-triazol-1-yl-methyl)silane.

7. A composition for controlling fungus diseases consisting essentially of a compound of claim 1 and at least one of the following: surfactant, solid or liquid inert diluent.

8. A composition for controlling fungus diseases consisting essentially of a compound of claim 2 and at least one of the following: surfactant, solid or liquid inert diluent.

9. A composition for controlling fungus diseases consisting essentially of a compound of claim 3 and at least one of the following: surfactant, solid or liquid inert diluent.

10. A composition for controlling fungus diseases consisting essentially of a compound of claim 4 and at least one of the following: surfactant, solid or liquid inert diluent.

11. A composition for controlling fungus diseases consisting essentially of a compound of claim 5 and at least one of the following: surfactant, solid or liquid inert diluent.

12. A composition for controlling fungus diseases consisting essentially of the compound of claim 6 and at least one of the following: surfactant, solid or liquid inert diluent.

13. A method for controlling fungus diseases which comprises applying to a locus to be protected an effective amount of a compound of claim 1.

14. A method for controlling fungus diseases which comprises applying to a locus to be protected an effective amount of a compound of claim 2.

15. A method for controlling fungus diseases which comprises applying to a locus to be protected an effective amount of a compound of claim 3.

16. A method for controlling fungus diseases which comprises applying to a locus to be protected an effective amount of a compound of claim 4.

17. A method for controlling fungus diseases which comprises applying to a locus to be protected an effective amount of a compound of claim 5.

18. A method for controlling fungus diseases which comprises applying to a locus to be protected an effective amount of the compound of claim 6.

* * * * *